United States Patent
Wang

(10) Patent No.: US 8,348,106 B2
(45) Date of Patent: Jan. 8, 2013

(54) FLUID DISPENSING OR FEEDING DEVICE

(76) Inventor: Hong Jen Wang, Kaohsiung (TW)

( * ) Notice: Subject to any disclaimer, the term of this patent is extended or adjusted under 35 U.S.C. 154(b) by 271 days.

(21) Appl. No.: 12/804,072

(22) Filed: Jul. 13, 2010

(65) Prior Publication Data
US 2012/0012618 A1    Jan. 19, 2012

(51) Int. Cl.
*B65D 88/54* (2006.01)
(52) U.S. Cl. ........ 222/333; 222/340; 222/386; 222/529; 222/648; 604/85; 604/251
(58) Field of Classification Search ............ 222/333.34, 222/648, 386, 529, 327, 63; 604/85, 251
See application file for complete search history.

(56) References Cited

U.S. PATENT DOCUMENTS

| | | | | |
|---|---|---|---|---|
| 1,871,989 A | * | 8/1932 | Heitger | 137/115.02 |
| 3,468,257 A | * | 9/1969 | Kofink | 417/415 |
| 3,790,028 A | * | 2/1974 | Gardner et al. | 222/129.4 |
| 4,124,146 A | * | 11/1978 | Sealfon | 222/641 |
| 4,808,089 A | * | 2/1989 | Buchholtz et al. | 417/417 |
| 4,883,467 A | * | 11/1989 | Franetzki et al. | 604/152 |
| 7,455,658 B2 | | 11/2008 | Wang | |
| 7,516,873 B2 | | 4/2009 | Wang | |
| 7,584,872 B2 | | 9/2009 | Wang | |

* cited by examiner

*Primary Examiner* — Frederick C. Nicolas
(74) *Attorney, Agent, or Firm* — Charles E. Baxley

(57) ABSTRACT

A fluid dispensing device includes a pressurizing device coupled between a fluid bottle and a discharge tube for forcing the fluid to flow through the discharge tube without gravity, the pressurizing device includes a container having an inclined inner peripheral surface, and a piston slidably received in the container and having an outer peripheral portion for selectively engaging with the inclined inner peripheral surface of the container in order to pump the fluid into the discharge tube when the piston is moved toward the discharge tube with a coil, and for being selectively disengaged from the inner peripheral surface of the container when the piston is moved away from the discharge tube.

1 Claim, 1 Drawing Sheet

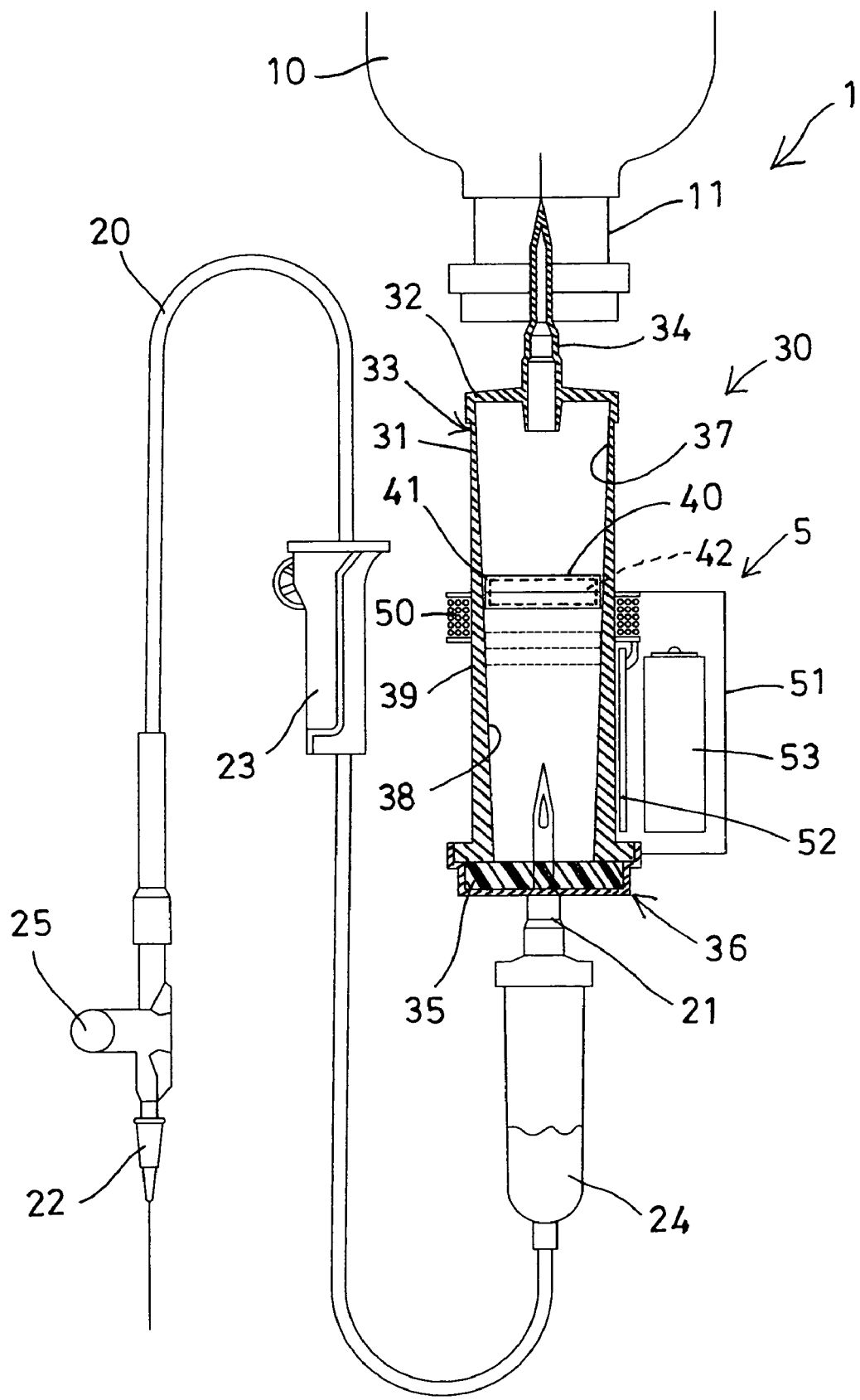

FLUID DISPENSING OR FEEDING DEVICE

BACKGROUND OF THE INVENTION

1. Field of the Invention

The present invention relates to a fluid dispensing or feeding device, and more particularly to a fluid dispensing or feeding device including a pressurizing device for pressurizing a fluid and for allowing a fluid bottle to be disposed below hearts of patients or users, and thus for allowing the fluid dispensing or feeding device to be easily carried by the patients or users.

2. Description of the Prior Art

Typically, fluid dispensing or feeding devices have been developed and provided for feeding or injecting medicinal fluids intravenously into human body tissue, and comprise a feed tube having a hypodermic needle provided on one end thereof for engaging into a fluid bottle or container, and having an injection needle provided on the other end thereof, for penetrating into patient's body tissue and for the purposes of injecting the fluid as desired.

For example, U.S. Pat. No. 7,455,658 to Wang, U.S. Pat. No. 7,516,873 to Wang, and U.S. Pat. No. 7,584,872 to Wang, were all developed by the present applicant and disclose several examples of the fluid dispensing devices each also including a pressurizing device coupled between a bottle and a discharge tube for forcing the fluid to flow through the discharge tube without gravity, in which the pressurizing device includes a container coupled between the bottle and the discharge tube, a piston slidably received in the container, and a motor coupled to the piston to move the piston in the reciprocating action within the container.

However, a complicated coupling mechanism is required to be provided and coupled between the motor and the piston for actuating or operating the piston to pump or to pressurize the fluid, and includes a lot of parts or elements that may not be easily manufactured and assembled.

The present invention has arisen to mitigate and/or obviate the afore-described disadvantages of the conventional fluid dispensing or feeding devices.

SUMMARY OF THE INVENTION

The primary objective of the present invention is to provide a fluid dispensing or feeding device including a pressurizing device for pressurizing a fluid and for allowing the fluid bottle to be disposed below hearts of patients or users, and thus for allowing the fluid dispensing or feeding device to be easily carried by the patients or users.

The other objective of the present invention is to provide a fluid dispensing or feeding device including a simplified structure or mechanism for allowing the fluid dispensing or feeding device to be made with a suitably reduced or decreased manufacturing cost and a simplified assembling procedure.

In accordance with one aspect of the invention, there is provided a fluid dispensing device comprising a bottle for receiving fluid therein, a discharge tube, a pressurizing device coupled between the bottle and the discharge tube for pressurizing the fluid and for forcing the fluid to flow through the discharge tube without gravity, the pressurizing device including a container coupled between the bottle and the discharge tube and having an inclined inner peripheral surface, a piston slidably received in the container and having an outer peripheral portion for engaging with the inner peripheral surface of the container, and the outer peripheral portion of the piston being engageable with the inner peripheral surface of the container in order to force the fluid into the discharge tube when the piston is moved toward the discharge tube, and the outer peripheral portion of the piston being disengaged from the inner peripheral surface of the container and to allow the fluid to flow through a gap between the inner peripheral surface of the container and the outer peripheral portion of the piston when the piston is moved away from the discharge tube, and a coil attached to the housing to act and to move the piston in a reciprocating action within the container in order to pump or force the fluid to flow from the bottle and then to flow through the discharge tube without gravity and for allowing the fluid bottle to be disposed below hearts of patients or users, and thus for allowing the fluid dispensing or feeding device to be easily handled or carried by the patients or users.

The pressurizing device includes at least one magnetic member engaged in the piston for acting with the coil and for allowing the piston to be moved up and down relative to the container and to be moved or driven in a reciprocating action within the container by the action between the coil and the magnetic members. One or more batteries may further be provided and coupled to the coil to energize and actuate the coil.

Further objectives and advantages of the present invention will become apparent from a careful reading of the detailed description provided hereinbelow, with appropriate reference to the accompanying drawings.

BRIEF DESCRIPTION OF THE DRAWINGS

FIG. 1 is a partial cross sectional view illustrating the operation of a fluid dispensing or feeding device in accordance with the present invention.

DETAILED DESCRIPTION OF THE PREFERRED EMBODIMENT

Referring to the drawing FIG. 1, a fluid dispensing or feeding device 1 in accordance with the present invention comprises a fluid container or bottle 10 for receiving fluids, such as medicinal fluids to be fed or injected intravenously into human body tissue, and a delivery or discharge tube 20 having a hollow hypodermic needle 21 provided on one end thereof for coupling to the bottle 10, and having an injection needle 22 provided on the other end thereof, for penetrating into patient's body tissue and for the purposes of injecting the fluid as desired. A clamp valve 23 is attached onto the flexible discharge tube 20 so as to control the dispensing or the rate of flow of the fluid in the well known manner.

Also positioned in the discharge tube 20 and located near the hollow hypodermic needle 21 or the bottle 10 is a drip meter or flow indicating device 24 usually made of transparent material for allowing the drops of fluid passing from the bottle 10 to the discharge tube 20 to be observed. An air relief valve 25 may further be provided and attached to the discharge tube 20, and preferably disposed close to the injection needle 22, for selectively relieving air, and for preventing air from being injected into human body tissue inadvertently, when no fluid is forced to flow through the discharge tube 20.

The fluid dispensing or feeding device 1 includes a pressurizing device 30 attached to or coupled between the bottle 10 and the discharge tube 20, for pressurizing the fluid and for allowing the fluid to flow through the discharge tube 20 despite of the gravity, and thus for allowing the fluid bottle 10 to be disposed below the hearts of the patients or users, and thus for allowing the fluid dispensing or feeding device 1 to be easily carried by the patients or users at any suitable position.

The pressurizing means or device 30 includes a container 31 having a cap 32 attached to one end or upper portion 33 thereof, and a hollow hypodermic needle 34 provided on or attached onto or extended from the cap 32, for engaging into the bottle neck portion 11 of the bottle 10, and thus for receiving the fluid from the bottle 10.

The container 31 includes a resilient plug 35 attached to the other end or lower portion 36 thereof, for blocking or enclosing the other end or lower portion 36 of the container 31. The hollow hypodermic needle 21 of the discharge tube 20 is to be engaged through the resilient plug 35 and into the container 31, for allowing the fluid to flow out of the fluid container 31 and to flow through the discharge tube 20. The resilient plug 35 is preferably made of such as rubber or synthetic materials for resiliently clamping or engaging with the hollow hypodermic needle 21 and for making a water tight seal between the fluid container 31 and the hollow hypodermic needle 21.

The pressurizing device 30 further includes a piston 40 slidably received in an inner chamber 37 of the container 31 and movable up and down relative to the container 31, and the piston 40 is made of soft or resilient rubber or plastic materials and includes a substantially planar or rectangular structure having a softer or resilient outer peripheral portion 41 for engaging with an inner peripheral surface 38 of the container 31, and the inner peripheral surface 38 of the container 31 is tapered or inclined or narrowed from the upper portion 33 or the middle portion 39 toward the middle portion 39 or the lower portion 36 of the container 31 for forming a cone or frustum-shaped inner peripheral surface 38 in the container 31 and for suitably engaging with the outer peripheral portion 41 of the piston 40.

The outer diameter of the piston 40 is greater than the inner diameter of the inner peripheral surface 38 at the middle portion 39 or the lower portion 36 of the container 31 for allowing the outer peripheral portion 41 of the piston 40 to be selectively engaged with the inner peripheral surface 38 of the container 31, and to allow the piston 40 to force the fluid toward the plug 35 and into the discharge tube 20 through the hollow hypodermic needle 21 when the piston 40 is moved toward the plug 35 or away from the cap 32, in addition, outer diameter of the piston 40 is smaller than the inner diameter of the inner peripheral surface 38 at the middle portion 39 or the upper portion 33 of the container 31 for allowing the outer peripheral portion 41 of the piston 40 to be selectively disengaged from the inner peripheral surface 38 of the container 31, and to allow the fluid to flow through the gap or passage between the inner peripheral surface 38 of the container 31 and the outer peripheral portion 41 of the piston 40 when the piston 40 is moved away from the plug 35 or toward the cap 32.

The pressurizing device 30 further includes an actuating device 5 having a coil 50 provided and attached to the container 31, such as attached to the middle portion 39 of the container 31, and disposed or supported or arranged around the pinion 40, and includes one or more magnetic members 42 disposed or engaged into the piston 40 for acting with the coil 50 and for allowing the piston 40 to be moved up and down relative to the container 31 and to be moved or driven in a reciprocating action within the container 31 by the action between the coil 50 and the magnetic members 42. A casing 51 is provided on or attached onto or extended from the container 31 for receiving or supporting the coil 50 and/or a circuit board 52 and/or one or more batteries 53 which may further be provided and coupled to the coil 50 and/or the circuit board 52 in order to energize and actuate the coil 50.

In operation, when the piston 40 is moved or driven toward the plug 35 or away from the cap 32 by the coil 50 and the magnetic members 42, the fluid contained in the lower portion 36 of the container 31 may be forced to flow toward the plug 35 and to flow into the discharge tube 20 through the hollow hypodermic needle 21, such that the fluid may be pressurized by the coil 50 and the magnetic members 42 and may be forced to flow through the discharge tube 20 without gravity, such that the fluid bottle 10 may be disposed below the hearts of the patients or users, and thus such that the fluid dispensing or feeding device 1 may be easily carried by the patients or users.

On the contrary, when the piston 40 is moved or driven away from the plug 35 or toward the cap 32 by the coil 50 and the magnetic members 42, the fluid contained in the upper portion 33 of the container 31 may flow through the gap or passage between the inner peripheral surface 38 of the container 31 and the outer peripheral portion 41 of the piston 40 and may then flow into the lower portion 36 of the container 31, for being forced to flow into the discharge tube 20 again when the piston 40 is moved or driven toward the plug 35 or away from the cap 32 by the coil 50 and the magnetic members 42 again, such that the fluid may be pressurized by the coil 50 and the magnetic members 42 in a reciprocating action, and may be controlled and forced to flow through the discharge tube 20 without gravity. The pumping mechanism of the container 31 and the piston 40 includes a simplified structure or configuration for allowing the fluid dispensing or feeding device 1 to be made with a suitably reduced or decreased manufacturing cost and a simplified assembling procedure.

The coil 50 and the magnetic members 42 and the piston 40 and/or clamp valve 23 and/or the flow indicating device 24 may be suitably arranged to control the dispensing or the rate of flow of the fluid through the discharge tube 20, and to prevent the fluid from being over pressurized. The coil 50 and the magnetic members 42 may be controlled or actuated by a switch (not shown) or the like. The other control device (not shown) may be used to control or to adjust or to change the operating speed of the coil 50 and the magnetic members 42 and/or the piston 40 and/or the rate of flow of the medicine fluid into the patient's body tissue.

Accordingly, the fluid dispensing or feeding device in accordance with the present invention includes a pressurizing device for pressurizing the fluid and for allowing the fluid bottle to be disposed below hearts of patients or users, and thus for allowing the fluid dispensing or feeding device to be easily carried by the patients or users, and includes a simplified structure or mechanism for allowing the fluid dispensing or feeding device to be made with a suitably reduced or decreased manufacturing cost and a simplified assembling procedure.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A fluid dispensing device comprising:
    a bottle for receiving fluid therein,
    a discharge tube,
    a pressurizing device coupled between said bottle and said discharge tube for pressurizing the fluid and for forcing the fluid to flow through said discharge tube without gravity, said pressurizing device including a container coupled between said bottle and said discharge tube and having an inclined inner peripheral surface, a piston slidably received in said container and having an outer peripheral portion for engaging with said inner peripheral surface of said container, and said outer peripheral portion of said piston being engageable with said inner peripheral surface of said container in order to force the fluid into said discharge tube when said piston is moved toward said discharge tube, and said outer peripheral portion of said piston being disengaged from said inner peripheral surface of said container and to allow the fluid to flow through a gap between said inner peripheral surface of said container and said outer peripheral portion of said piston when said piston is moved away from said discharge tube, and said pressurizing device including at least one magnetic member engaged in said piston, a coil attached to said container to act with said at least one magnetic member of said piston and to move said piston in a reciprocating action within said container, and at least one battery coupled to said coil.

* * * * *